US00PP37289P2

(12) United States Plant Patent
Hansen

(10) Patent No.: US PP37,289 P2
(45) Date of Patent: Feb. 24, 2026

(54) ***LAVANDULA* PLANT NAMED 'Summer Serenade'**

(50) Latin Name: *Lavandula angustifolia*
Varietal Denomination: Summer Serenade

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/831,568

(22) Filed: Apr. 25, 2025

(51) Int. Cl.
*A01H 5/02* (2018.01)

(52) U.S. Cl.
USPC ..... Plt./445

(58) Field of Classification Search
USPC ..... Plt./445
CPC ..... A01H 6/502; A01H 5/02; A01H 6/50
See application file for complete search history.

*Primary Examiner* — Keith O. Robinson

(57) ABSTRACT

A new and unique cultivar of *Lavandula* plant named 'Summer Serenade' that is medium-sized, dense, mounded, well-branched, upright, winter-hardy, perennial habit. The new plant begins flowering early, is freely-flowering without requiring vernalization, and has flowers of dark lavender with calyxes of moderate violet-blue on densely branched panicles. The new plant has excellent vigor, is resistant to deer and rabbits, and is useful in the landscape and as a cut flower.

1 Drawing Sheet

Botanical denomination: *Lavandula angustifolia.*
Variety designation: 'Summer Serenade'.

STATEMENT REGARDING PRIOR DISCLOSURES UNDER 37 CFR 1.77(B)(6)

The first offer for sale of *Lavandula* 'Summer Serenade' was privately made by Walters Gardens, Inc. to Bell Nursery on May 16, 2024. The new plant has also been advertised online by North Shore Plant Club but as of the application date has not been sold by North Shore Plant Club. North Shore Plant Club and Walters Gardens, Inc. obtained the new plant and information about the new plant directly or indirectly from the inventor. Walters Gardens, Inc. has not publicly offered the new plant. No plants of *Lavandula* 'Summer Serenade' have been sold, in this country or anywhere in the world, nor has any disclosure of the new plant been made, more than one year prior to the filing date of this application, and such sale or disclosure within one year was either derived directly or indirectly from the inventor and would be a 35 U.S.C § 102(b) exception.

BACKGROUND OF THE INVENTION

The present invention relates to a new and distinct *Lavandula* plant from the genus *Lavandula* and given the cultivar name 'Summer Serenade'. The new plant was a single seedling selection from a self-pollination on Aug. 15, 2021, by the inventor of a proprietary, oryzalin-treated, selected sport (not patented) of 'SuperBlue' U.S. Plant Pat. No. 24,929 that was treated with oryzalin. The seeds were collected in the late summer of 2021 and sown on Dec. 6, 2021. The individually selected seedling was eventually given the breeder code 21-11-2 after being first isolated from trials at a wholesale perennial nursery in Zeeland, MI during the summer of 2022. The new plant was selected for final introduction in the summer of 2023.

*Lavandula* 'Summer Serenade' has been asexually propagated since 2022 at the same nursery in Zeeland, MI using basal shoot tip cuttings and found to reproduce plants that are identical and exhibit all the characteristics of the original plant in successive generations of asexual propagation.

The new plant, *Lavandula* 'Summer Serenade', has not been observed under all possible environments. The phenotype may vary slightly with different environmental conditions, such as temperature, light, fertility, moisture, and maturity levels, but without any change in the genotype.

In comparison, the parent is taller and more upright in habit, has longer inflorescences with less branching, and the flowers are smaller.

The nearest comparison varieties known to the inventor are: 'Essence Purple' (not patented), 'Hidcote' (not patented), 'Imperial Gem', 'Munstead' (not patented), 'Kerlavangem' U.S. Plant Pat. No. 23,001, and 'SuperBlue'.

'Essence Purple' has a taller habit, with less branching, and longer inflorescences with a softer shade of blue flowers. 'Imperial Gem' has a shorter habit and the flowers have smaller lobes and are more violet-colored. 'Hidcote' has a less dense habit. 'Munstead' has a smaller and shorter habit and the flower spikes are shorter with fewer flowers. 'Kerlavangem' has a slightly broader habit with plump violet-purple flowers on slightly taller spikes. 'SuperBlue' has a smaller habit, the flower buds are smaller and the petals are a strong violet.

*Lavandula* 'Summer Serenade' differs from the above cultivars and all other plants known to the inventor with the following combined traits:

1. Medium-sized, dense, well-branched, upright, habit;
2. Freely flowering without requiring vernalization, with flowers of dark-lavender and calyxes of moderate violet-blue;
3. Early to flower with a long bloom time with effectiveness extended by heavily compound-branched panicles;

4. Excellent vigor, good winter hardiness, and resistance to deer and rabbits.

BRIEF DESCRIPTION OF THE DRAWINGS

The drawings are of two-year-old plants in mid-season flower in a trial block at a nursery in Zeeland, Michigan and demonstrate the overall appearance of the new plant, including its unique traits. The colors are as accurate as reasonably possible with color reproductions. Ambient light spectrum, temperature, source, and direction may cause the appearance of minor variations in color.

DETAILED PLANT DESCRIPTION

Figure 1:
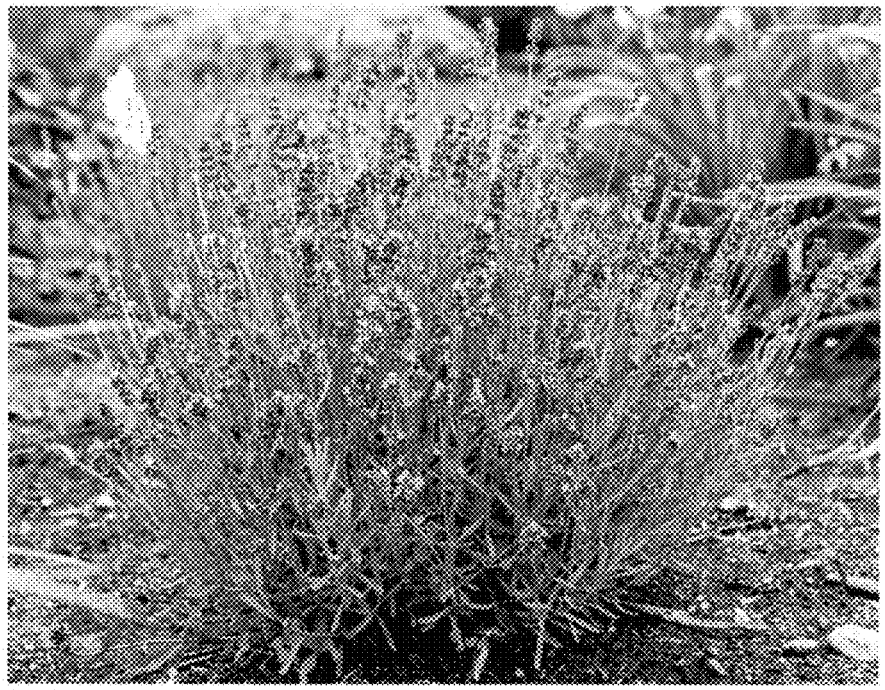
FIG. 1 shows a side view of two-year-old plants in mid-season flower in a trial block at a nursery in Zeeland, Michigan.
Figure 2:
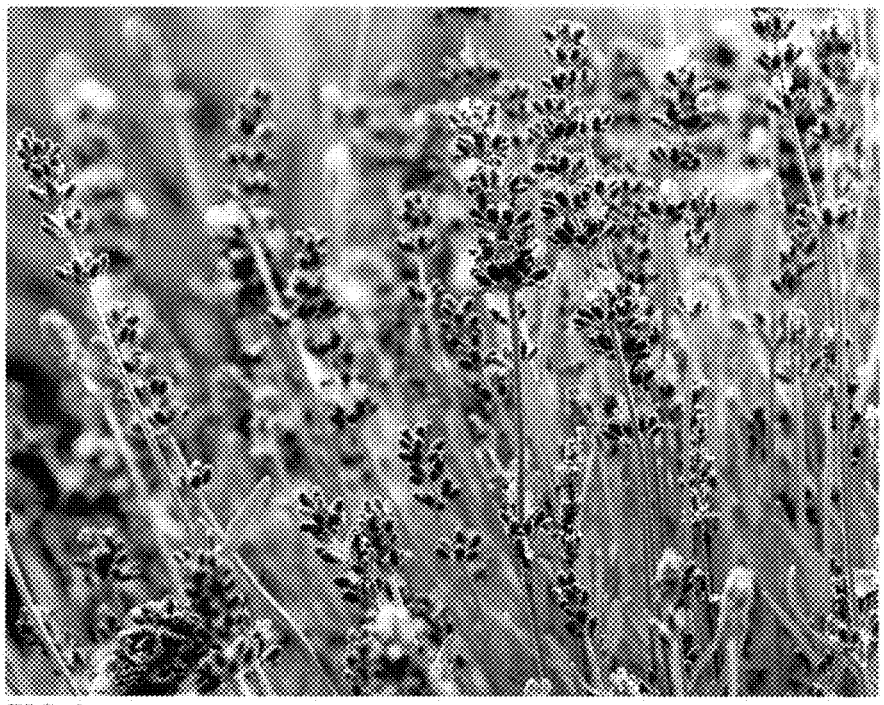
FIG. 2 shows a close-up of a peduncle branch with flowers, buds, and calyxes.

The following is a detailed description of the new *Lavandula* 'Summer Serenade' based on observations of two-year-old specimens grown in a trial garden at a wholesale perennial nursery in Zeeland, MI. Color descriptions are from the 2015 edition of The Royal Horticultural Society Colour Chart except where common dictionary terms are used.

Plant habit: Multi-stemmed semi-woody perennial, with rounded, heavily branched outline; flowering in the upper 40 cm;

Plant size: Flowering to about 51 cm tall and 50 cm wide;

Roots: Fibrous, well-branched; to about 2 mm diameter near base; color near white to light tan depending on soil type and mineral content, RHS NN155B to RHS 161D;

Stem: Cylindrical; woody, smooth and glabrous in lower portion; heavily branched; upper portion quadrangular, stiff, wiry, argenteous, and asperous; to about 5 mm across at base in woody portion; and 45 cm long with flowering starting about 10 cm above soil; individual stems with about 15 internodes below branched peduncle; internodes average about 11 mm long, greater distally; about 12 main stems per plant with about 6 to 8 branches per main stem;

Branches: Opposite; quadrangular; about 80 primary branches per plant; to about 41 cm long and about 2 mm diameter at base;

Stem color: Main stem base portions nearest RHS 199D and nearest RHS 160C; young distal branch color between RHS 147D and RHS 148D;

Leaf: Simple; opposite and decussate; linear; sessile; base cuneate and truncate; apex rounded; margin entire; both adaxial and abaxial surfaces argenteous and asperous; number of leaves per stem about 16 to 20;

Leaf fragrance: Strongly herbal lavender, aromatic;

Leaf size: To about 45 mm long and 6 mm wide near middle;

Leaf color: Young expanding adaxial and abaxial between RHS 191A and RHS 191B; mature adaxial nearest RHS 191A, mature abaxial between RHS N138B and RHS 191B;

Leaf venation: Pinnate; not obvious adaxial; argenteous, asperous, and slightly costate abaxial;

Vein color: Expanding adaxial veins not obvious, expanding abaxial midrib nearest RHS 146D and primary veins not obvious; mature adaxial midrib nearest RHS 146D in the proximal one-quarter and distally between RHS N138B and RHS 191B, mature abaxial midrib and primary veins between RHS N138B and RHS 191B;

Petiole: Sessile;

Inflorescence: Spike with dense verticils; about 80 to 120 flowers and about 7 whorls per peduncle, and up to 800 flowers per branched stem; flowering portion about 20 cm long and about 4 cm across; total stem flowering portion about 40 cm long and about 11 cm across; each stem flowering for about 5 weeks;

Bloom period: Early July through early fall in Zeeland, Michigan;

Peduncle: Average about 20 cm tall and about 1.5 mm at base of flowers; argenteous and asperous; aspect stiffly upwardly;

Peduncle color: Between RHS N138B and RHS 191B;

Pedicel: Cylindrical; short; argenteous and asperous; attitude mostly outwardly; from 0.5 to about 2 mm long and 0.7 mm diameter; color nearest RHS 190C;

Flower: Perfect; complete; zygomorphic; sympetalous; bilabiate; with five sympetalous petals forming a 2-lobed upper lip and 3-lobed lower lip; attitude outwardly to slightly upwardly;

Flower size: About 10 mm long, about 6 mm across; corolla to about 9 mm long, 6 mm across, tube about 3 mm diameter at fusion of two lips; aspect mostly outwardly;

Flower period: Spike in flower for about three weeks; individual flowers open for about three days; and entire plant flowering from early summer to fall;

Bud one day prior to opening: Elliptical; about 9 mm long, calyx about 2.5 mm diameter, and petal portion about 2 mm diameter;

Bud color: Exposed petals nearest RHS N82D at base, in the distal exposed petals between RHS N88B and RHS N88C, and the calyx nearest RHS 83A distally and the calyx base nearest RHS 145D;

Petals: Glabrous adaxial except micro-puberulent in fused corolla portion; glabrous abaxial; upper and lower petals proximally fused forming tube in the basal 7 mm long and 3 mm diameter toward fusion of the two petals; both petals matte in both adaxial and abaxial;

Upper labium: 2-lobed; about 10 mm long and 5 mm across toward apex; lobes centrally cleft about 1 mm deep and 3 mm across; lobe apices rounded; margin entire;

Lower labium: 3-lobed; about 9 mm long, center and side lobes to 2.5 mm long and 2 mm wide, apices rounded with entire margins;

Petal color: Distal adaxial upper and lower labium upon first opening and fully open between RHS N87B and RHS N87C; and distal abaxial upper and lower labium upon first opening and fully open nearest RHS 86D; adaxial and abaxial when first opening and when fully open proximal 3 mm of corolla tube nearest NN155B;

Calyx: Campanulate; to about 6 mm long and diameter about 4 mm at apex;

Sepals: Five; linear; acute apices; entire margin; to about 6 mm long and 1 mm wide at fusion, fused into tube in basal 5 mm; puberulent abaxial and glabrous inside; matte both surfaces;

Sepal color: Adaxial nearest RHS 148C with veins nearest RHS 137B, abaxial proximally nearest RHS 86A; with pubescence nearest RHS N87A;

Gynoecium: Single; to 5 mm long; not exerted; superior;

*Style*.—One; about 3 mm long and about 0.2 mm diameter; terete; glabrous; mostly straight; lustrous; color nearest RHS 155C.

*Stigma*.—Oblong; about 1 mm long and about 0.3 mm diameter; color nearest RHS 22C.

*Ovary*.—Superior; globose; about 1 mm diameter; color nearest RHS 145B.

Androecium: In two sets of two, not exerted;

*Filaments*.—Two longer and two shorter; paired and exerted; adnate to the corolla; longer pair to 4.5 mm long and adnate in the basal 4 mm and free in the proximal 0.5 mm; shorter pair to 4 mm long and adnate in the basal 3.5 mm and free in the proximal 0.5 mm; color both sets nearest RHS NN155C.

*Anthers*.—Dorsifixed; versatile; longitudinal; globose; to about 0.7 mm diameter; color nearest RHS 20A.

*Pollen*.—Not yet observed.

Fragrance: None detected different than foliage fragrance;

Fruit and seeds: Not yet observed;

Resistance: 'Summer Serenade' shows no susceptibility to *Odocoileus, Sylvilagus*, or *Oryctolagus* browsing but has not been tested or shown resistance to other pests and diseases common to *Lavandula.*

Hardiness: The new plant has survived USDA hardiness zones 5 to 9 but has not been tested yet beyond these temperatures.

I claim:

1. A new and distinct cultivar of *Lavandula* plant named 'Summer Serenade' as herein described and illustrated.

* * * * *